United States Patent [19]

Matsumoto et al.

[11] Patent Number: 5,040,069

[45] Date of Patent: Aug. 13, 1991

[54] ELECTRONIC ENDOSCOPE WITH A MASK BUMP BONDED TO AN IMAGE PICK-UP DEVICE

[75] Inventors: Seiji Matsumoto; Makoto Shiino, both of Omiya, Japan

[73] Assignee: Fuji Photo Optical Co., Ltd., Omiya, Japan

[21] Appl. No.: 528,488

[22] Filed: May 25, 1990

[30] Foreign Application Priority Data

Jun. 16, 1989 [JP] Japan .................................. 1-152154
Jun. 16, 1989 [JP] Japan .................................. 1-152155
Jun. 16, 1989 [JP] Japan .................................. 1-152156

[51] Int. Cl.$^5$ ........................ H04N 3/14; H04N 5/335
[52] U.S. Cl. .................................. 358/213.11; 358/98; 358/229; 358/209
[58] Field of Search ................... 358/98, 213.11, 209; 357/80, 74, 79; 250/239, 578.1

[56] References Cited

U.S. PATENT DOCUMENTS 4,594,613 6/1986 Shinbori et al. ................. 358/213.11
4,745,470 5/1988 Yabe et al. ............................ 358/98
4,757,805 7/1988 Yabe ......................................... 128/6

FOREIGN PATENT DOCUMENTS 63-66525 3/1988 Japan .

Primary Examiner—Howard W. Britton
Assistant Examiner—Tuan V. Ho
Attorney, Agent, or Firm—Oblon, Spivak, McClelland, Maier & Neustadt

[57] ABSTRACT

Described herein is a solid image pickup assembly for use in an electronic endoscope, including a substrate having a mask defining a masked area bearing wiring patterns and an image pickup area in the form of a light transmitting window, and a solid image pickup device. Also, the solid image pickup device is mounted on the substrate with the light receiving surface thereof in alignment with the transparent window by directly bump bonding electrodes of the image pickup device to the corresponding electrodes on the part of the substrate.

5 Claims, 6 Drawing Sheets

ELECTRONIC ENDOSCOPE WITH A MASK BUMP BONDED TO AN IMAGE PICK-UP DEVICE

BACKGROUND OF THE INVENTION

1. Field of the Invention

This invention relates to a solid image-pickup assembly particularly suitable for use in medical and industrial electronic endoscopes.

2. Description of the Prior Art

Electronic endoscopes generally have a solid image pickup device or imager such as a CCD fitted in the tip end of an insert portion to be introduced into a body. The solid image pickup device is usually supplied in the form of a solid image pickup assembly which has the image pickup device mounted on a wiring substrate and received in a package with a transparent protective glass window for transmission of incident light. The solid image pickup assembly is fixedly mounted in an objective lens barrel. The wiring substrate for mounting the solid image pickup device is flat in shape and has predetermined wiring patterns formed thereon. The wiring portions on the substrate are connected with the electrode portions on the surface of the solid image pickup device by wire bonding means.

In the case of a bronchoscope to be inserted into the bronchus, for example, its insert portion is required to be as small as possible in diameter and to contain a rigid portion of as small a length as possible. In order to meet these requirements, the solid image pickup assembly to be incorporated into the insert portion has to be small enough in size. Recently, there have been developed solid image pickup devices which are markedly improved in the degree of integration, more specifically, which are formed with ten thousands to hundred thousands picture elements on an extremely small chip of about 1-2 mm. The use of such a small device should contribute to the reduction in size of the solid image pickup assembly.

However, as mentioned hereinbefore, the actual use of a small-size solid image pickup device does not necessarily result in a corresponding reduction in size of the solid image pickup assembly as a whole, which has a triple-layer construction including a wiring substrate, a solid image pickup device mounted on the wiring substrate and protective glass covering the light receiving surface of the image pickup device. In addition, the electrodes which are formed on the front side of the solid image pickup device have to be connected to the electrodes on the wiring substrate by wire bonding means through interconnecting wires which are projected in an arch-like fashion. Therefore, it is necessary to provide a clearance of a certain width between the light receiving surface of the solid image pickup device and the protective glass. This results in an increased thickness of the solid image pickup assembly as a whole, making it difficult to shorten the length of the rigid portion at the tip end of the insert portion. Besides, the wire bonding itself requires to extend the interconnecting wires over a certain distance in a direction parallel with the face of the image pickup device, barring the reduction of the wiring substrate dimensions as well as the reduction of the diameter of the insert portion.

ABSTRACT OF THE DISCLOSURES

With the foregoing situations in view, the present invention has as its object the provision of a compact small-size solid image pickup assembly particularly suitable for use in electronic endoscopes.

In accordance with the present invention, for achieving the above-stated object, there is provided a solid image pickup assembly which essentially includes: a substrate having a transparent window formed thereon by a masking member to define an image pickup region and wiring patterns formed on masked regions; and a solid image pickup device having the light receiving surface thereof disposed in face to face relation with the transparent window of the substrate and being connected with electrodes on the substrate by bump bonding.

BRIEF DESCRIPTION OF THE DRAWINGS

The above and other objects, features and advantages of the invention will become apparent from the following description and the appended claims, taken in conjunction with the preferred embodiments shown in the accompanying drawings, which are given for the purpose of illustration only and, needless to say, should not be construed as limitative of the invention.

In the accompanying drawings:

FIGS. 1 through 6 show a first embodiment of the invention, of which,

FIG. 1 is a sectional view of a tip end portion of the insert portion of an endoscope;

FIG. 2 is an exploded perspective view of a solid image pickup assembly;

FIG. 3 is a sectional view taken on line III—III of FIG. 1;

FIG. 4 is an outer view of a substrate, taken from the back side thereof;

FIG. 5 is a plan view of a solid image pickup device; and

FIG. 6 is a diagrammatic illustration explanatory of the process of forming a solid image pickup assembly;

FIGS. 7 and 8 show a second embodiment of the invention, of which,

FIG. 7 is an exploded perspective view of a solid image pickup assembly; and

FIG. 8 is a diagrammatic illustration of a thin film substrate construction; and FIGS. 9 to 11 show a third embodiment of the invention, of which, FIG. 9 is an exploded perspective view of a solid image pickup assembly;

FIG. 10 is a plan view of the image forming side of a transparent substrate; and FIG. 11 is a plan view of the object side of the transparent substrate.

DESCRIPTION OF PREFERRED EMBODIMENTS

Figure 1:
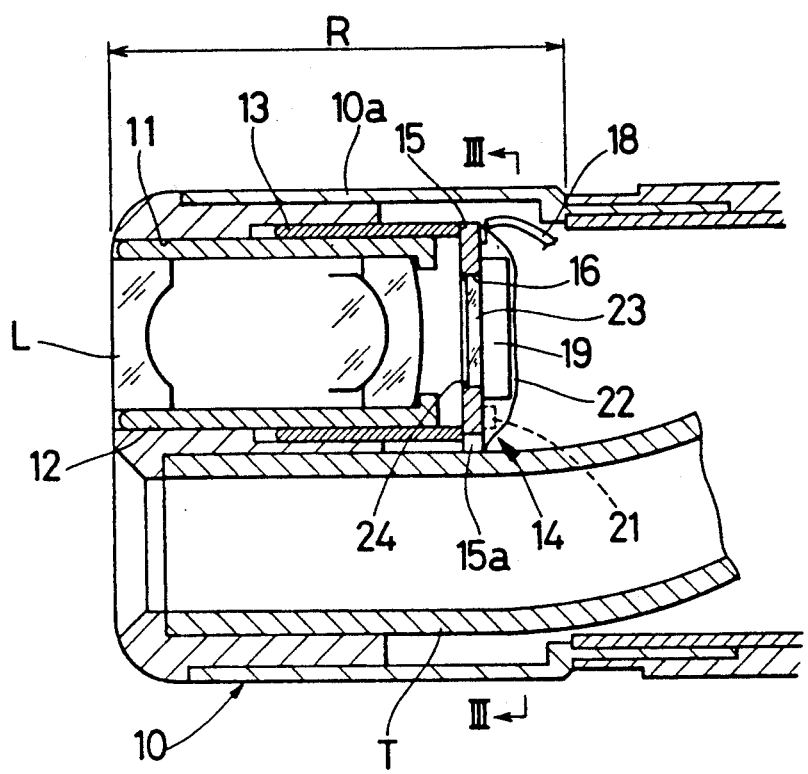

Hereafter, the invention is described more particularly by way of the preferred embodiments shown in the drawings.

Shown schematically in FIG. 1 is the construction of a tip end portion of an insert portion of an electronic endoscope, wherein indicated at 10 is a tip member secured to the fore end of the insert portion and provided with a through hole 11 for fittingly receiving therein an optical unit including inner and outer cylinders 12 and 13 of the lens barrel which supports an objective lens L. A solid image pickup assembly 14 is securely attached to the inner end of the inner cylinder 12 of the lens barrel to serve as an image pickup means.

Figure 2:
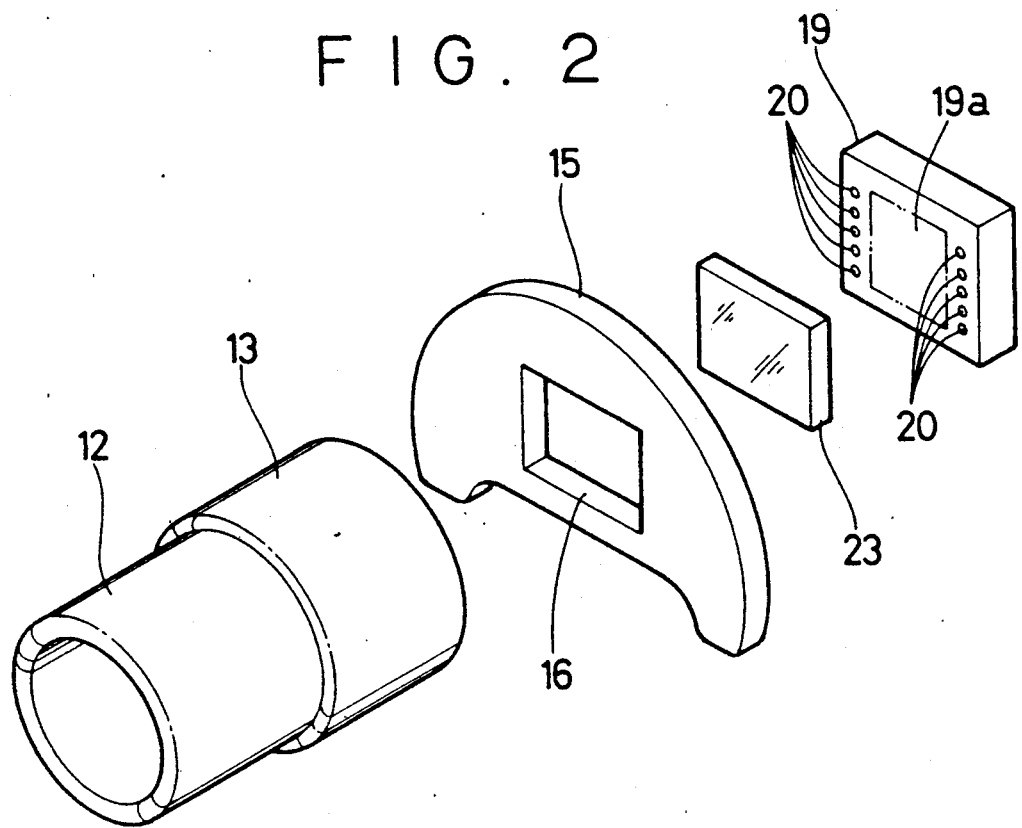
Figure 3:
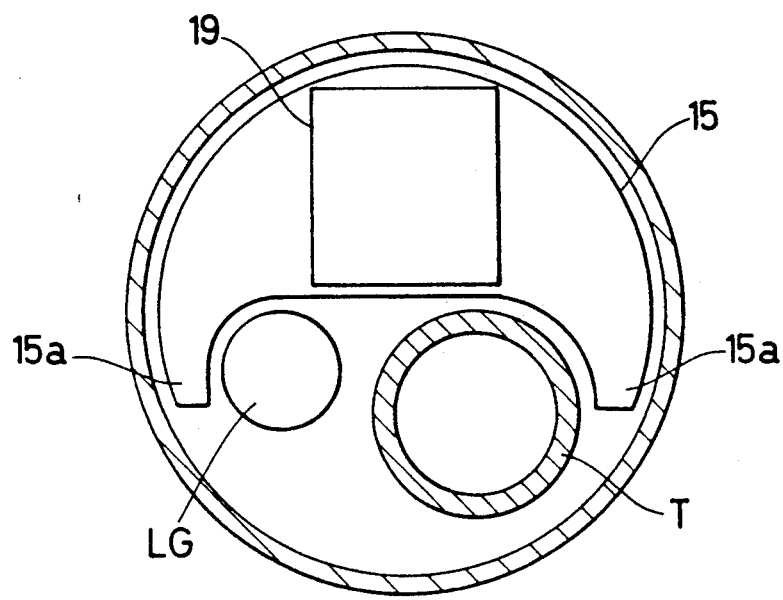
Figure 4:
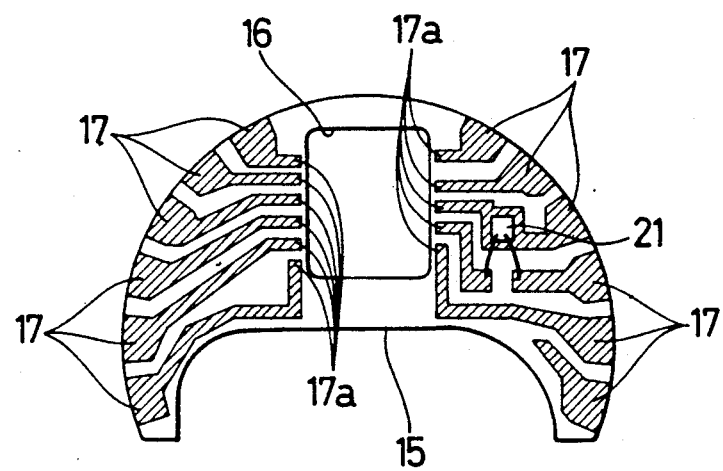

The solid image pickup assembly 14 has a construction as shown particularly in FIGS. 2 and 3. In these figures, the reference 15 indicates a substrate of insulating material such as ceramics or the like, which is centrally provided with a rectangular opening 16. On the rear side, the substrate 15 is formed with predetermined wiring patterns 17 as shown in FIG. 4, each wiring pattern being connected to a wiring cable 18 at the outer peripheral marginal edge of the substrate 15 and having an electrode portion 17a in the vicinity of the center opening 16.

Figure 5:
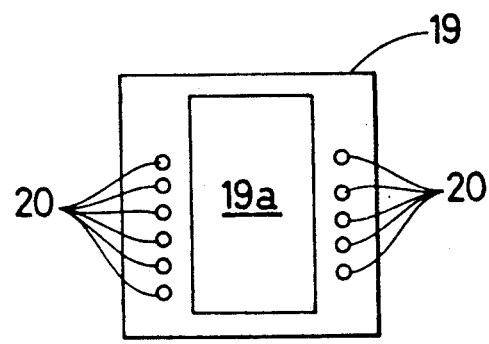

A solid image pickup device 19 is mounted on the rear side of the substrate 15. As clear from FIG. 5, the solid image pickup device 19 is centrally provided with a light receiving surface 19a between rows of a large number of electrodes 20. Facing the light receiving surface 19a toward the opening 16, the electrodes 20 of the solid image pickup device 19 are directly bonded to the electrode portions 17a of the wiring patterns 17 on the substrate 15.

For bonding the electrodes 20 and 17a together, bumps of indium alloy, solder, conductive adhesive or the like are used. Bumps are formed either on the electrodes 20 of the solid image pickup device 19 or on the electrode portions 17a of the substrate wiring patterns 17 (the electrodes 20 are formed to have a bump electrode structure in this particular embodiment). The solid image pickup device 19 is positioned on the substrate 15 such that the bumps of the electrodes 20 are exactly in registration with the substrate electrodes 17a, and then the bumps are fused under heating condition to bond the electrodes 20 and 17a together by the so-called bump bonding.

On the side away from the light receiving surface, the solid image pickup device 19 is provided with overflow drain electrodes, which are connected to the substrate 15 by wire bonding or alternatively by bump bonding if desired. The substrate 15 is adapted to mount a buffer amplifier 21 on its rear side.

The solid image pickup device 19 which has been mounted on the substrate 15 in this manner is covered in a sealed state under a sealing synthetic resin material such as epoxy resin or the like. For the purpose of protecting the light receiving surface 19a of the solid image pickup device 19, a transparent protective member 23 such as a sheet of flat optical glass or a transparent synthetic resin 23 is fitted in the center opening 16 through a sealing material 24 which seals off the peripheral edge portions of the transparent protective member 23. Consequently, the solid image pickup element 19 is retained in a sealed state.

The substrate 15 is formed substantially in a semi-circular shape and provided with lower extensions 15a at the opposite ends thereof to secure a broad substrate area for the wiring patterns 17 without interfering with instrument insertion channel T, light guide LG or other components which are built in or inserted into the insert portion of the endoscope.

Figure 6:
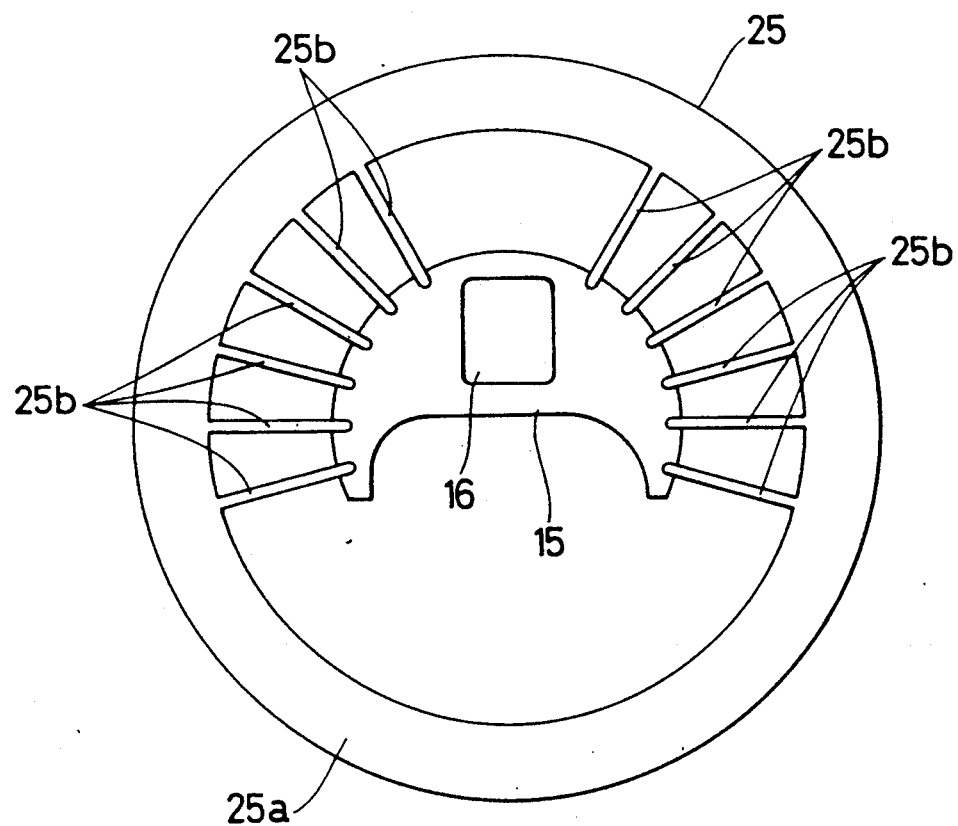

In the present embodiment with the above-described arrangements, the solid image pickup device assembly 14 is formed firstly by the use of a lead frame 25 as shown in FIG. 6, bonding a plural number of radially arranged lead members 25b on a rim portion 25a of the lead frame 25 to the respective wiring patterns on the substrate 15. By so doing, the wiring cable 18 is connected to the substrate 15. In this instance, the use of the lead frame 25 serves to simplify the wiring patterns 17 to be formed on the substrate 15, and therefore to reduce the surface area of the substrate 15. Consequently, it becomes possible to reduce the outer diameter of the solid image pickup assembly 14 while facilitating the connection of the substrate to the cable to a marked degree.

In the next place, the solid image pickup device 19 is located in position on the rear side of the substrate 15, holding the light receiving surface 19a in alignment with the opening 16 and registering the respective electrodes 20 with the corresponding electrode portions of the wiring patterns 17. The thus registered electrodes are heated under pressure, whereupon the bump electrode portions are fused to bond the electrodes 20 and 17a together. At this time, since the solid image pickup device 19 is normally provided with the electrodes 20 on the front side which faces the wiring patterns 17 on the rear side of the substrate 15, the electrodes 20 and 17a can be connected directly to each other without resorting to the wire bonding means.

After completing the connections between the substrate and the solid image pickup device 19, a synthetic resin seal 22 is applied to the rear side of the substrate 15 in such a manner as to cover the solid image pickup device 19, and the transparent protective member 23 is fitted in the opening 16 through the seal material 24 which stops the gap around the protective member 23, thereby retaining the solid image pickup device 19 in sealed state for protection while preventing electric disconnections between the electrodes 20 and 17a.

Nextly, the rim portion 25a of the lead frame 25 is cut off, and the outer free ends of the lead portions 25b are folded rearward. The solid image pickup device assembly 14 thus formed is mounted within the tip section 10 by securely fixing the front side of the substrate 15 to the inner end of the barrel 13 of the objective lens L with use of bonding or other suitable fixation means, and connecting a cable to the ends of the lead portions 25b.

In this manner, the solid image pickup device 19 is directly connected to the substrate 15 across the center opening 16 by bump bonding without using interconnecting wires, so that the solid image pickup assembly 14 can be formed in a thickness substantially corresponding to the combined thickness of the substrate 15 and the solid image pickup device 19. Accordingly, the dimensions including the thickness of the solid image pickup assembly 14 can be reduced markedly as compared with the conventional counterpart of the triple-layer construction which is composed of a substrate, a solid image pickup device and a transparent protective member and which is required to provide a clearance between the solid image pickup device and the transparent protective member to accommodate the interconnecting wires which are projected from the solid image pickup device as a result of wire bonding. In addition, in contrast to the wire bonding which needs a certain extent of extra spaces on the substrate, the bump bonding of the substrate 15 and solid image pickup device 19 requires only a minimum substrate surface area which is necessary for forming the wiring patterns 17 and therefore permits to reduce also the areal dimensions of the substrate 15. Consequently, it becomes possible to reduce the diametral dimensions of the components contained in the insert portion and the diameter of the insert portion itself.

As is well known in the art, an angle portion and a flexible portion are successively connected to the rigid tip member 10 at the distal end of the insert portion of the endoscope. Namely, the rigid portion R which cannot bend itself along the path of insertion is extended as far as the inner end of a rigid sleeve member 10a which is provided in such a manner as to circumvent the solid image pickup assembly 14 for protection thereof. The reduction in thickness of the solid image pickup assembly 14 makes it possible to reduce the axial length of the sleeve 10a and thus the dimensions of the rigid portion R. Especially in case of an endoscope, the reduction in length of the rigid portion R, even if it is smaller than 1 mm, has an extremely great importance in manipulation of the endoscope, for example, for facilitating the observation of an infected area when inserted into a narrow bronchus or the like.

Further, in order to obtain images of satisfactory quality from the solid image pickup device 19, the light receiving surface of the solid image pickup device 19 has to be confined only to the light which contributes to the imaging and shielded from other unnecessary light. For example, in case of a frame transfer type CCD which is constituted by image and storage areas, the picture quality is degraded by blooming unless the storage areas are completely shielded from light. Accordingly, it is necessary to provide a shielding means which prevents incidence of unnecessary light on the light receiving surface of the solid image pickup device 19.

In this regard, the solid image pickup device 19 which is mounted on the substrate 15 substantially in an intimately contacting relation with the rear side of the substrate 15 is completely shielded from light except the areas corresponding to the opening 16. It follows that, when the opening 16 is formed in an appropriate shape, it functions as a masking plate for preventing incidence of unnecessary light on the solid image pickup device 19.

Figure 7:
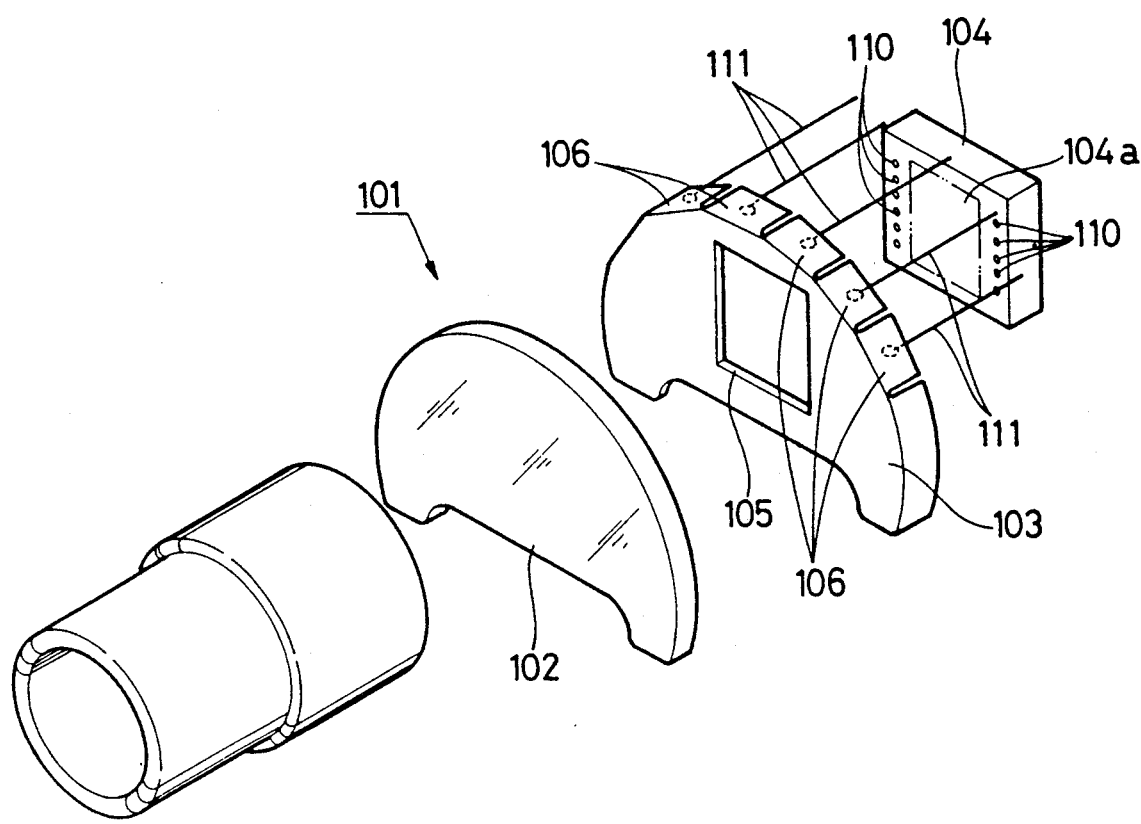
Figure 8:
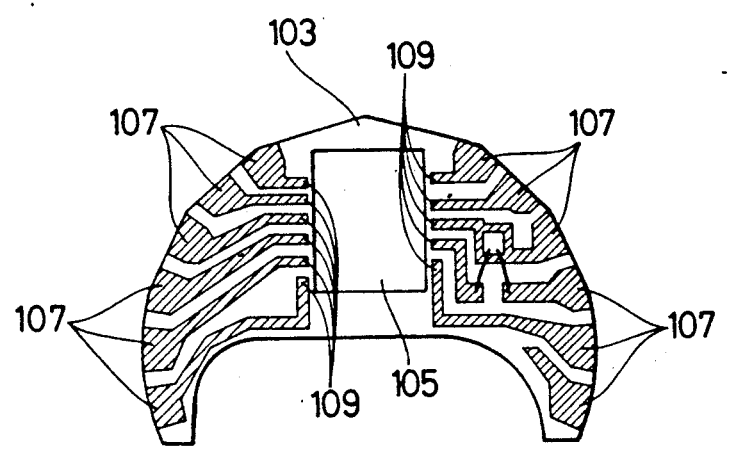

FIGS. 7 and 8 illustrate a second embodiment of the invention, in which, as seen particularly in FIG. 7, a solid image pickup assembly 101 is constituted by a transparent support plate 102 of optical glass or other material, a flexible thin film substrate 103 consisting of a resin film or the like and bonded to one side of the support plate 102, and a solid image pickup device 104 mounted on the thin film substrate 103. The thin film substrate 103 blocks light except in the area of a rectangular opening 105 which is provided centrally in the substrate 103. Further, the thin film substrate 103 is provided with a plural number of flap portions 106 which are extended radially outward of the peripheral edge of the transparent support plate 102 and folded backward.

As shown in FIG. 8, wiring patterns 107 which are formed on the surface of the thin film substrate 103 are extended onto the folded flap portions 106 and connected to cables 111. The wiring patterns 107 are provided with electrode portions 109.

The solid image pickup device 104 is mounted on the rear side of the thin film substrate 103 with the wiring patterns 107, facing the light receiving surface 104a toward the opening 105. Electrodes 110 which are provided on the part of the solid image pickup device 104 are registered with and connected to the electrode portions 109 by bump bonding. The flap portions 106 of the thin film substrate 103 are folded back toward the solid image pickup device 104 and connected to cables 111.

This arrangements permit to make the solid image pickup assembly more compact and smaller in size. The thin film substrate 103 likewise functions as a masking member for preventing incidence of unnecessary light on the solid image pickup device 104.

Figure 9:
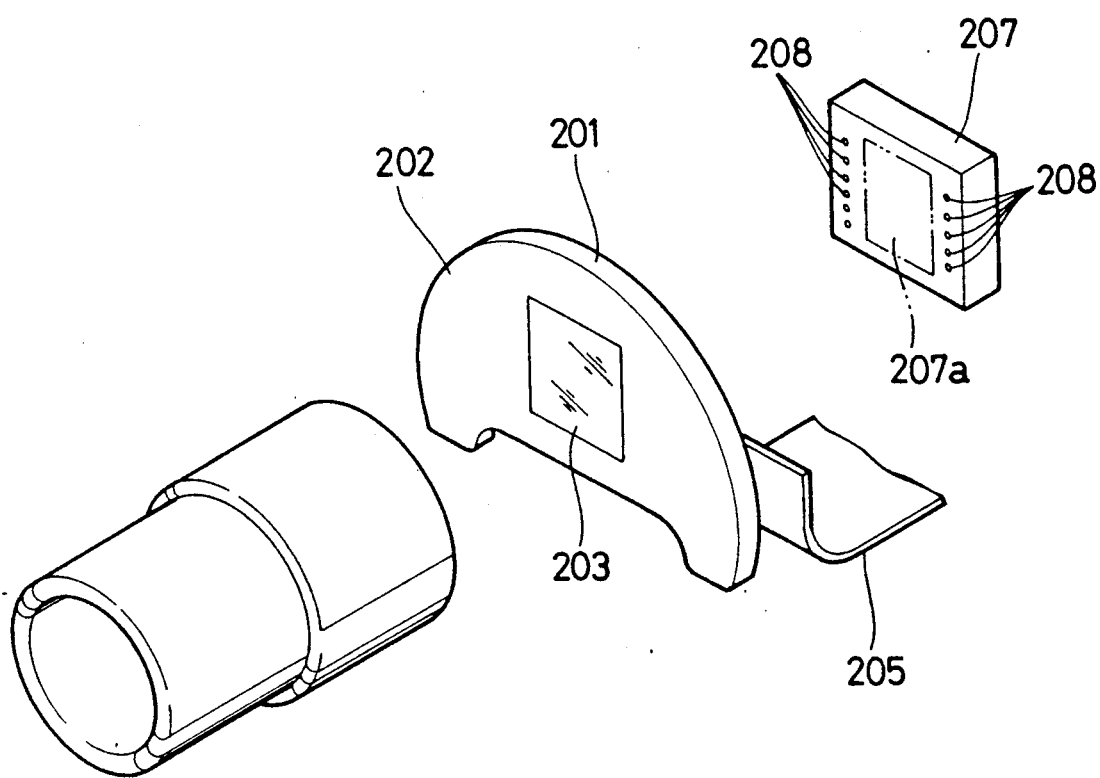
Figure 10:
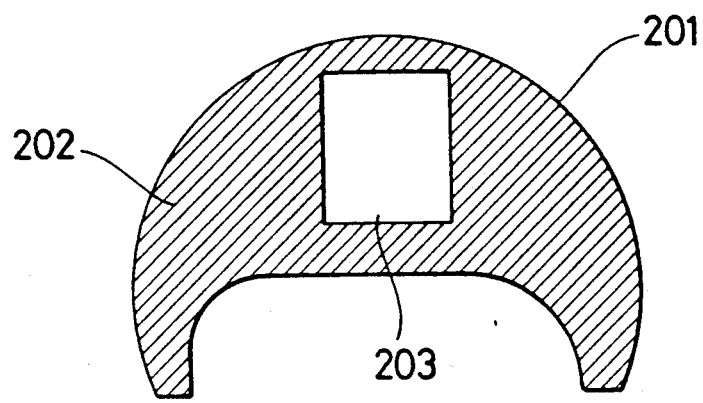
Figure 11:
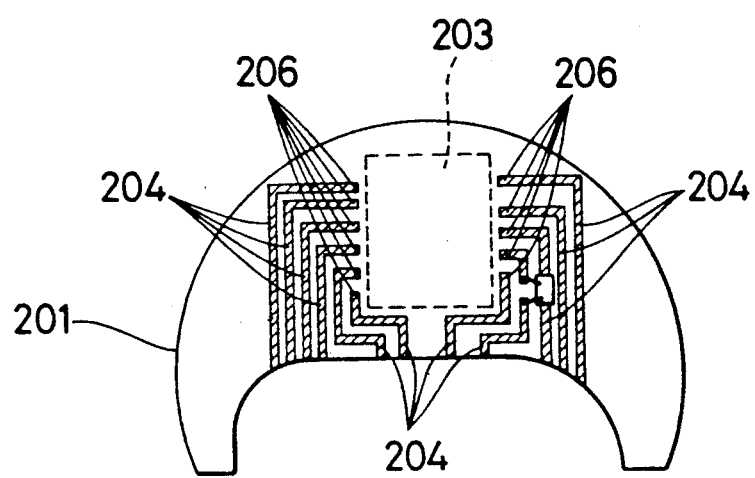

Referring to FIGS. 9 to 11, there is shown a third preferred embodiment of the invention, which employs a transparent substrate 201 of a flat glass sheet in the insert portion of an electronic endoscope. A masking layer 202 is formed on one side of the transparent substrate 201 to define light-blocking areas as indicated by hatching in FIG. 10, leaving a rectangular light transmitting window 203 in a center portion of the transparent substrate 201.

A plural number of wiring patterns 204 are formed on the other side of the substrate 201 as shown in FIG. 11, in the areas which are masked by the masking layer 202. A flat flexible wiring board 205 is connected to the respective wiring patterns 204 to lead them out to a suitable position. The wiring patterns 204 are provided with electrode portions 206 in the same manner as in the foregoing embodiments.

The solid image pickup device 207 is bonded through bumps to the rear side of the transparent substrate 201 bearing the wiring patterns 204, with the light receiving surface 207a in alignment with the window 203 and with the electrodes 208 in registration with the electrode portions 206 on the part of the transparent substrate 201.

This arrangement is substantially the same as the above-described first and second embodiments in operation and resulting effects.

What is claimed is:

1. A solid image pickup assembly for use in an electronic endoscope comprising:
   a solid image pickup device having an image pickup area and electrodes on the same surface;
   a substrate having a masking means defining an image pickup area in the form of a light transmitting transparent window;
   said masking means bearing a wiring pattern and electrodes on a surface opposite to said image pickup device; and
   at least one electrode of said image pickup device and at least one respective electrode of said masking means being bump bonded to one another.

2. A solid image pickup assembly as defined in claim 1, wherein said substrate is composed of an opaque substrate sheet having an opening in said image pickup area and a transparent sheet fitted in said opening.

3. A solid image pickup assembly as defined in claim 1, wherein said substrate is composed of a transparent support member and a thin film substrate member adhered to said transparent support member.

4. A solid image pickup assembly as defined in claim 1, wherein said substrate is composed of a transparent support member and a masking layer formed on one side of said transparent support member.

5. A solid image pickup assembly as defined in claim 3, wherein said thin film substrate member is provided with peripheral extensions projecting outward from peripheral edge portions of said transparent support member, said wiring patterns being extended to said peripheral extensions for connection to a cable.

* * * * *